(12) United States Patent
Boursier Niutta et al.

(10) Patent No.: US 7,437,906 B2
(45) Date of Patent: Oct. 21, 2008

(54) FLOW REGULATOR DEVICE FOR AN ANALYTICAL CIRCUIT AND ITS USE IN CHROMATOGRAPHY

(75) Inventors: Stefano Boursier Niutta, Naples (IT); Michele Gentile, Porza (CH)

(73) Assignee: Dani Instruments S.p.A., Cologno Monzese (IT)

( * ) Notice: Subject to any disclaimer, the term of this patent is extended or adjusted under 35 U.S.C. 154(b) by 0 days.

(21) Appl. No.: 10/503,591

(22) PCT Filed: Feb. 22, 2002

(86) PCT No.: PCT/EP02/01903

§ 371 (c)(1),
(2), (4) Date: Mar. 22, 2005

(87) PCT Pub. No.: WO03/071265

PCT Pub. Date: Aug. 28, 2003

(65) Prior Publication Data

US 2005/0155409 A1    Jul. 21, 2005

(51) Int. Cl.
*G01N 30/32* (2006.01)
*G01N 30/86* (2006.01)
*F16K 31/64* (2006.01)

(52) U.S. Cl. .................. 73/23.27; 73/23.42; 95/15; 137/12

(58) Field of Classification Search ................. 73/23.27, 73/23.42; 137/12, 14; 95/15; 96/421
See application file for complete search history.

(56) References Cited

U.S. PATENT DOCUMENTS

| | | | |
|---|---|---|---|
| 3,174,326 A | | 3/1965 | Carle et al. |
| 3,240,052 A | * | 3/1966 | Reinecke et al. ........... 73/23.27 |
| 5,340,476 A | * | 8/1994 | Berger et al. ............. 210/198.2 |
| 5,363,874 A | * | 11/1994 | Henszey et al. ................ 137/14 |
| 5,476,000 A | * | 12/1995 | Henderson et al. ......... 73/23.27 |
| 5,711,786 A | * | 1/1998 | Hinshaw ......................... 95/82 |
| 5,938,817 A | * | 8/1999 | Shibamoto et al. ............. 95/23 |
| 5,952,556 A | * | 9/1999 | Shoji .......................... 73/23.42 |
| 6,490,910 B1 | * | 12/2002 | Butler et al. ................ 73/23.42 |
| 6,776,025 B2 | * | 8/2004 | Lechner-Fish ............. 73/23.41 |

FOREIGN PATENT DOCUMENTS

| | | |
|---|---|---|
| DE | 37 17 456 C1 | 7/1988 |
| EP | 0 685 738 A | 12/1995 |
| EP | 0 721 156 A | 7/1996 |
| WO | WO 98/52713 | 11/1998 |

* cited by examiner

*Primary Examiner*—Michael Cygan
(74) *Attorney, Agent, or Firm*—Hoffman, Wasson & Gitler

(57) ABSTRACT

A flow regulator device for an analytical circuit, characterised by comprising: a fluid restriction (R) of defined characteristics related to the field of application of the analytical circuit, a direct-pressure regulator (2) positioned upstream of said restriction (R), a back pressure regulator (4) positioned downstream of said restriction (R).

3 Claims, 4 Drawing Sheets

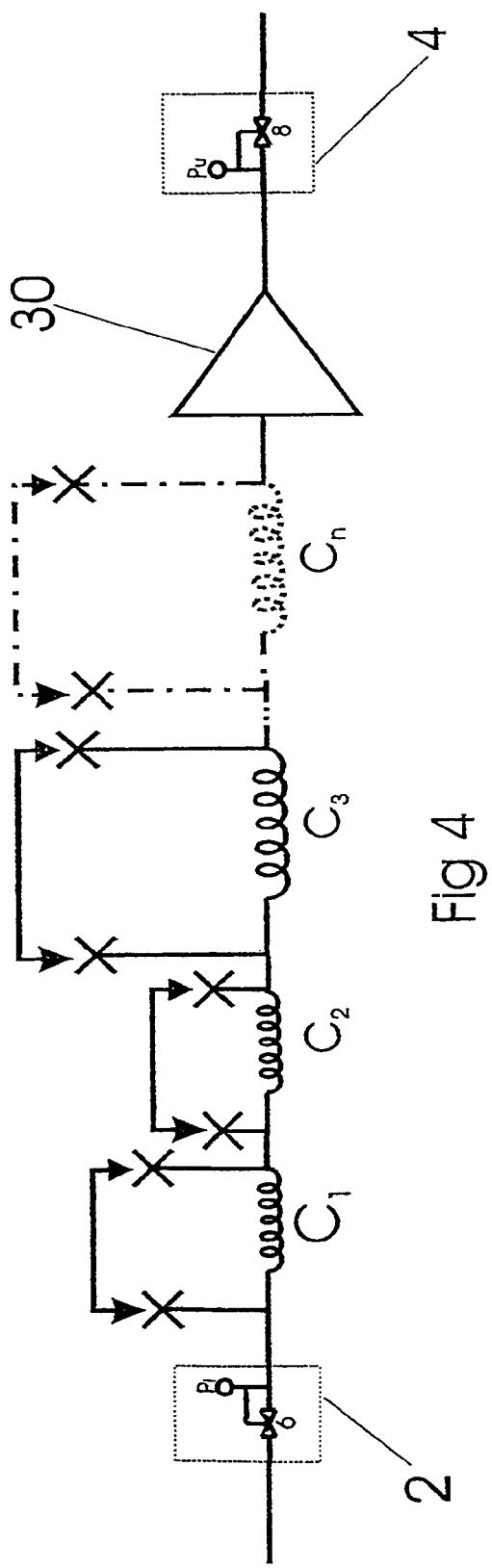

FLOW REGULATOR DEVICE FOR AN ANALYTICAL CIRCUIT AND ITS USE IN CHROMATOGRAPHY

This invention relates to a flow regulator device for an analytical circuit and its use in chromatography.

In the technical chromatography sector it is often required to control the flow through the analytical circuit, both in the sense of maintaining it constant and in the sense of varying it in the required manner for analytical purposes.

The requirement to maintain the flow constant during chromatographic analysis is related to the fact that the hydraulic column loads vary with varying temperature during analysis, the requirement to vary the flow in a required manner being instead related to the need to subject the sample to different analysis methods.

To control the flow through a column of an analytical circuit, a pressure regulator is currently used in series with the column. For this purpose a control program is provided which varies the gas pressure in such a manner as to compensate the column load variations, due for example to temperature variations, which in their turn are related for example to the analysis program.

A drawback of this system is the fact that it is strictly related to the column characteristics and does not provide a general solution to the problem, given the differences between one column and another.

An actual flow regulator in the form of a mass flow regulator is also known for connection upstream of the column. It is based on the cooling effect provided by a gas stream which strikes a hot filament. As the extent of the cooling effect depends on the gas flow, the flow can be controlled by controlling the temperature of said filament.

A drawback of this flow regulator is the fact that besides being sensitive to the gas flow it is also sensitive to the gas characteristics; the result is that a variation in the filament temperature does not only signify a variation in the flow rate of the gas to be analysed, but can also depend on a variation in the gas composition; consequently a regulator of this type cannot be used in an analytical circuit, the function of which is precisely to determine the gas composition.

An object of the invention is to provide a flow regulator device which is free of the aforesaid drawbacks.

Another object of the invention is to provide a flow regulator device which can be effectively used in circuits in which variations in the composition of the gas to be analysed may occur.

These and further objects which will be apparent from the ensuing description are attained, according to the invention, by a flow regulator device for an analytical circuit, as described in claim 1.

A preferred embodiment of the invention is described in detail hereinafter, together with some of its particular advantageous applications in the chromatographic field, with reference to the accompanying drawings, in which:

FIG. 4 shows schematically the use of the device of the invention in a multi-circuit analytical circuit to implement chromatograph switching.

Figure 1:
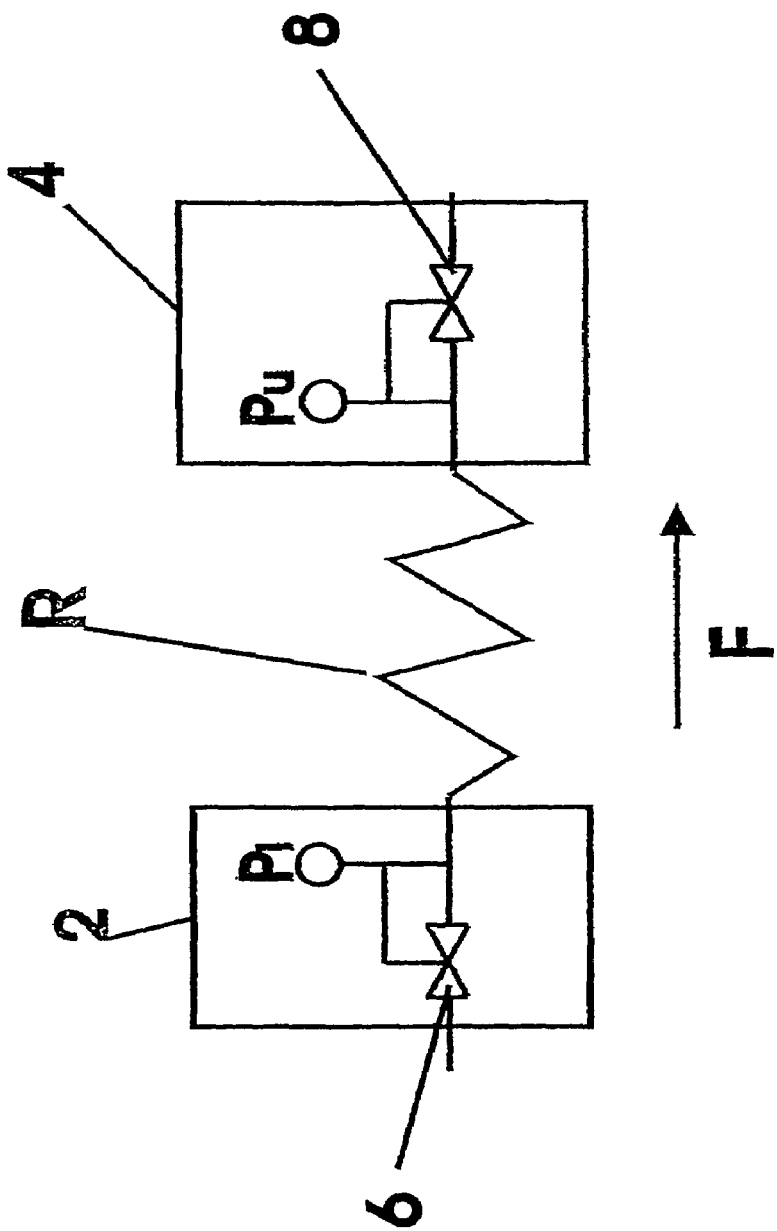
FIG. 1 is a schematic view of a device according to the invention.

As can be seen from the figures, the flow regulator device of the invention comprises a fluid restriction R of constant characteristics, which can consist for example of a piece of tube of length L and diameter D, presenting at its inlet end a pressure $P_i$ and at its outlet end a pressure $P_u \leq P_i$.

As is known from the Poiseuille equation, the flow F of a gas passing with very low linear velocity through the restriction R, across the ends of which there is a pressure difference $\Delta P = P_i - P_u$ is given by $$F = k(P_i^2 - P_u^2)/P_u$$

in which $k = k'D^4/\eta L$ where k' is a proportionality constant, D is the tube diameter, L its length and $\eta$ the gas viscosity.

The flow regulator of the invention uses at the ends of the restriction R two regulators 2 and 4 for regulating the pressures $P_i$ and $P_u$ at its respective ends.

More specifically, with reference to the flow direction F, the upstream regulator 2 is a direct regulator, whereas the downstream regulator 4 is a back-pressure regulator.

The direct regulator 2 is in the form of an electronically controlled proportional valve 6 able to reduce its port size when the pressure $P_i$ at the control point, which is positioned downstream of the valve, exceeds the set value. In this manner the valve 6 automatically returns the pressure $P_i$ to the set value.

The back-pressure regulator 4 is an electronically controlled proportional valve 8 able to increase its port size when the pressure $P_u$ at the control point, which is positioned upstream of the valve, exceeds the set value.

Again in this case the valve 8 automatically returns the pressure $P_u$ to the set value.

Different ways of electronically controlling the proportional valves 6 and 8 exist. One of these ways, advantageously usable in the device of the invention, is to use a program developed for processor Scorpion 128K Controller—5521 devised and marketed by Micro-Robotics Ltd, Cambridge.

By virtue of the aforedescribed circuit configuration, the pressure values $P_i$ and $P_u$ can be controlled independently, to hence, for equal temperatures, maintain a constant flow passing through the restriction R to determine the controlled pressure values at its ends.

With reference to FIG. 1, it is apparent that if the pressure $P_i$ falls below the set value, the valve 6 opens to a greater extent to pass an increased pressure and so restore equilibrium.

If instead the pressure $P_u$ decreases, the valve 8 closes to reduce the discharge from the measurement point to the outside, and again restore equilibrium.

The combined effect of the two independent adjustments enables the gas flow through the restriction R to be controlled by using two pressure controls and correct application of the Poiseuille equation (this in fact assumes different exemplifications in relation to the linear velocity of the gas).

It should be noted that the Poiseuille equation is in fact known for determining the value of a gas flow knowing the pressures across a circuit element traversed by said gas flow, however two pressure regulators of different type have never been used to regulate a gas flow.

Because of the facility for easily and at the same time accurately controlling a gas flow, the device of the invention is suitable for advantageous use in various chemical and industrial sectors, and in particular in typical chromatographic applications, such as in a standard throttling circuit, an electronic control circuit for a gas chromatography column split, and a control circuit for column switching in a multi-column analytical system.

Standard Throttling Circuit

In the chromatography field it is frequently required to obtain predetermined concentrations of gaseous sample (standard) at different concentrations but at rigorously constant flow rates, to be then used in quantitative determinations.

For this purpose a gas cylinder 10 is used, for example of methane in known standard concentration, for example 6 ppm, in helium.

Figure 2:
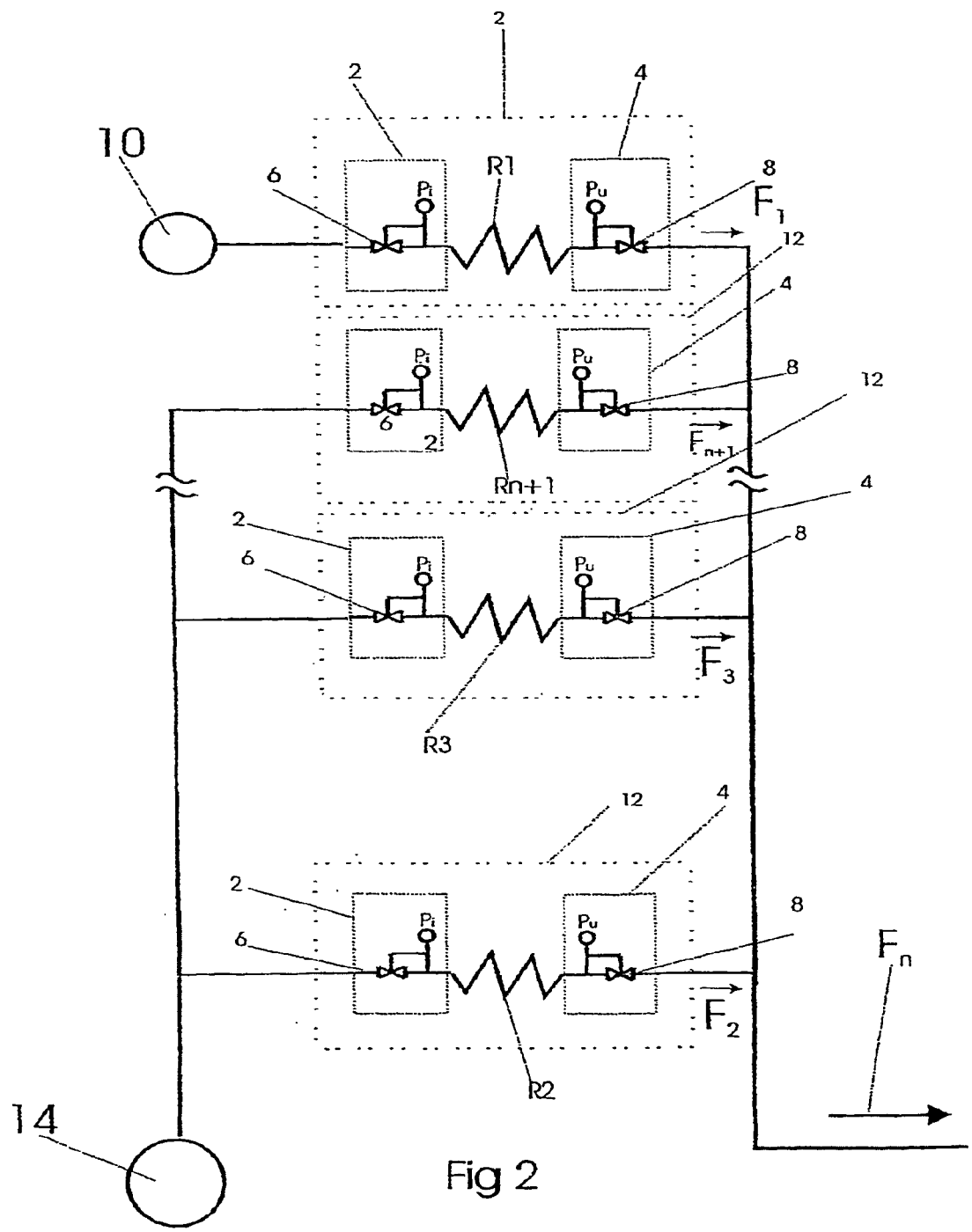
FIG. 2 shows schematically the use of a device of the invention to form a standard throttling circuit.

From the scheme of FIG. 2 it can be seen that the gas from the cylinder 10 passes through the device of the invention, indicated overall by 12 and comprising a restriction $R_1$ interposed between a direct-pressure regulator 2 upstream and a back-pressure regulator 4 downstream.

The characteristics of the restriction $R_1$ and the set values of the two pressures $P_{i1}$ and $P_{u1}$ are chosen such that the gas flow $F_1$, through the regulator device 12 is for example 200 ml/min.

The standard throttling circuit also comprises another cylinder 14 containing the actual gas in which the methane is dissolved, i.e. pure helium. From this cylinder there extend n separate branches passing through a further n flow regulator devices 12 of the invention, with n restriction $R_2$, $R_3$, ..., $R_{n+1}$.

Let $F_2$, $F_3$, ..., $F_{n+1}$ be the gas flow rates through these n devices 12.

For descriptive simplicity it will be assumed that the regulator devices 12 are equal and that hence the flow rates $F_1$, $F_2$, $F_3$, ..., $F_{n+1}$ are all equal to 200 ml/min, although this limitation is in no way essential.

If the flow rate leaving the throttling circuit is indicated by $F_u$ it is immediately apparent that if the n branches are closed, $F_u = F_1 = 200$ ml/min and the concentration of methane in helium is 6 ppm.

If one branch, for example that comprising the restriction $R_2$, is open and the other branches are closed, $F_u = F_1 + F_2 = 400$ ml/min and the concentration is 3 ppm.

If two branches, for example those comprising the restrictions $R_2$ and $R_3$, are open and the remainder are closed, $F_u = F_1 + F_2 + F_3 = 600$ ml/min and the methane concentration is 2 ppm. and so on.

Each branch can be closed by acting for example on the relative back-pressure regulator 4.

As there are also other branches, it is evident that by varying the number of these and by varying the characteristics determinable by each flow regulator, and starting from a single gas cylinder 10 of standard concentration, practically any lower standard concentration value can be obtained without having to vary the total flow rate.

Spit Control Circuit

Figure 3:
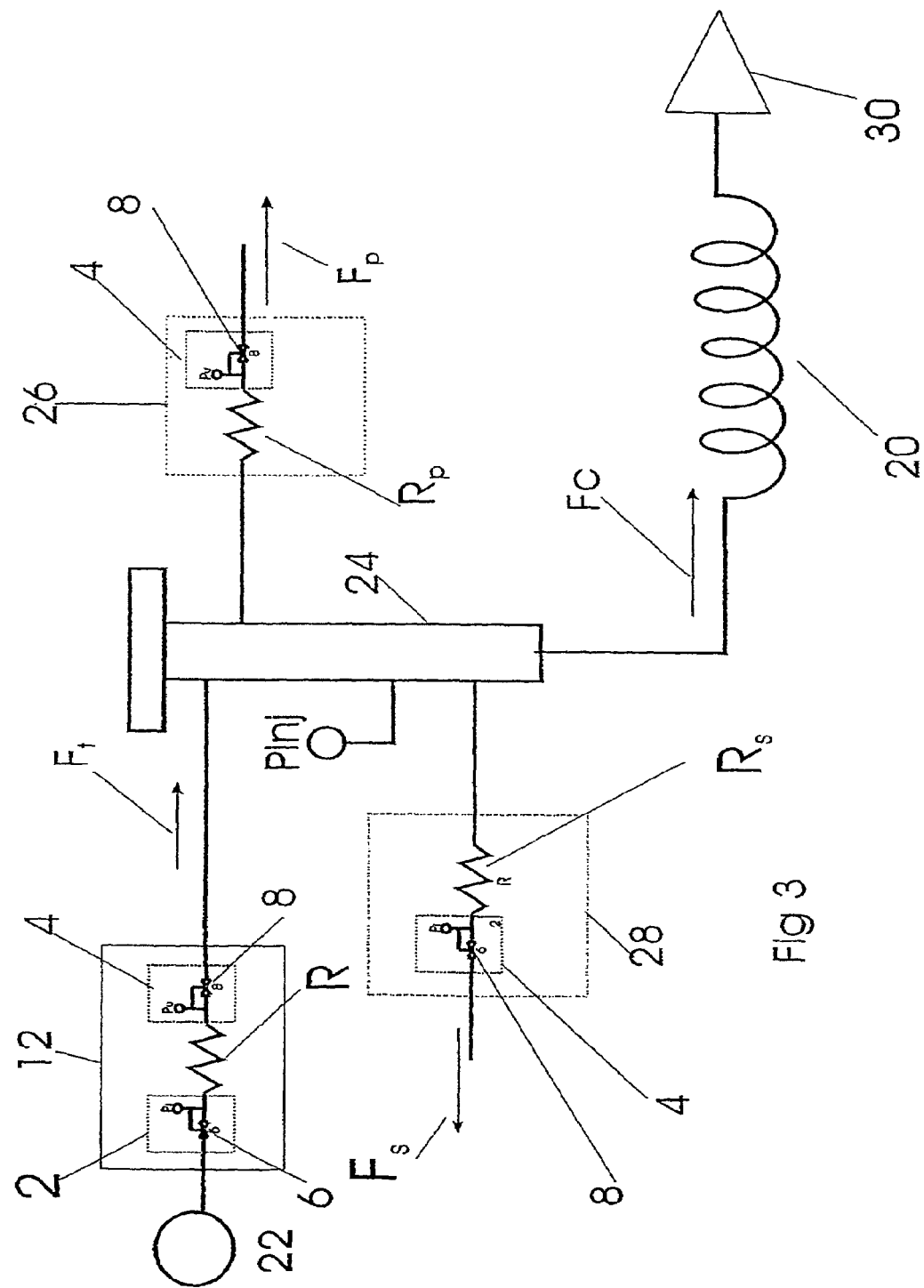
FIG. 3 shows schematically the use of devices of the invention to electronically control the split of a gas chromatograph.

FIG. 3 schematically illustrates an analytical circuit with a column 20 to be inserted into an oven for chromatographic analyses.

The circuit comprises a cylinder 22 of transport gas, a flow regulator device 12 according to the invention, an injector 24 into which the gas to be analysed is fed, a purge circuit 26 and a split circuit 28, these extending from the injector 24, and an analytical circuit comprising the analysis column 20 and an exit detector 30.

Both the purge circuit 26 and the split circuit 28 comprise a restriction $R_p$ and $R_s$ and a back-pressure regulator 4 positioned downstream of said restriction $R_p$ and $R_s$.

As a direct-pressure control $P_{inj}$ is provided within the injector 24, this forms with the two circuits 26 and 28 two regulator devices according to the invention.

In operation, the inlet regulator device controls the flow $F_T$, whereas the other two regulator devices 24-26 and 24-28 control the purge flow $F_p$ and the split flow $F_S$ respectively, and in this manner they also indirectly control the column flow $F_c$, which is not directly controllable because the components to be analyzed pass into the column in very small concentration, and it is easy to imagine contamination of these samples as they pass through regulator valves comprising gaskets.

Multi-Column Analytical Circuit

In gas chromatography it is often necessary to use analytical circuits comprising several columns, which have to be able to be excluded in those cases in which their presence could alter the use of others. Such circuits must therefore be provided with shut-off valves able to selectively exclude one or more columns, and they must at the same time be provided with means able to prevent, on excluding one or more columns, any modification in the gas flow rate through the non-excluded columns.

It follows that if column switching is effected in an analytical circuit on the basis of analytical requirements, this result in a circuit modification and a variation in the gas flow through the non-excluded columns. To preserve the original regime the pressure in the various parts of the circuit must be varied, with the result that the original conditions are restored with a certain transient delay, which in addition to slowing down the measurement can also result in its alteration because of possible loss of significant data during the transient phase.

Moreover in chromatographic analyses, in which sensors are used which are sensitive to variation in the gas flow to which they are exposed (for example TCD sensors), it is important that during the analysis there is no flow variation which could alter the measurements.

Consequently in multi-column analytical circuits, there is interest both in maintaining the transport gas pressure constant during column switching to prevent, or at least reduce, the said transients, and in maintaining the transport gas flow constant in order not to alter the sensor response.

Up to the present time this has been achieved either by using calibrated hydraulic restrictions, which hence have an excessive rigidity as their characteristics can in no way be modified, or by using needle valves adjustable manually by the operator, who must therefore be a person of adequate technical knowledge and reliable experience.

The multi-column analytical circuit illustrated in FIG. 4 effectively overcomes these limitations by the use of a flow regulator device according to the invention.

This circuit uses as the restriction R of the regulator device the actual multi-column analytical circuit $C_1 \ldots C_n$ itself, which is therefore interposed between the direct-pressure regulator 2 (upstream) and the back-pressure regulator 4 (downstream).

For the purposes of circuit operation, the circuit detector 30 can be positioned either upstream or downstream of the back-pressure regulator 4, even though for practically reasons it is advisable that it be positioned downstream to enable the two regulators 2 and 4 to remain outside the oven into which the analytical circuit $C_1 \ldots C_n$ has to be inserted.

This special use of the regulator device of the invention is particularly advantageous, in that it causes the detector 30 to operate at constant flow and at the same time the columns $C_1 \ldots C_n$ to operate at constant pressure; consequently all errors due to flow variations through the detector are eliminated, and at the same time, because of the elimination of transients in column switching, the time required for analytical analysis is substantially reduced enabling chromatograms to be obtained with considerable reduction in system errors.

The invention claimed is:

1. A flow regulator device for an analytical circuit, comprising:
   a fluid restriction,
   a direct-pressure regulator positioned immediately upstream of said restriction, and comprising a proportional valve controlled electronically on the basis of the pressure existing downstream of said valve, with reference to the direction of the flow passing through said fluid restriction
   a back pressure regulator positioned immediately downstream of said restriction and comprising a proportional valve controlled electronically on the basis of the pressure existing upstream of said valve, with reference to the direction of the flow passing through said fluid restriction.

2. A device as claimed in claim 1, wherein said fluid restriction comprises a piece of tube of constant diameter.

3. A flow regulator device for an analytical circuit, comprising:
   a fluid restriction,
   a direct-pressure regulator having a port and positioned immediately upstream of said restriction, the direct pressure regulator controlling the pressure entering the restriction, the direct-pressure regulator port becoming smaller when the pressure exceeds a preset value,
   a back pressure regulator having a port and positioned immediately downstream of said restriction, the back pressure regulator controlling the pressure leaving the restriction, the back pressure regulator port becoming larger when the pressure exceeds a preset value.

* * * * *